US005840490A

United States Patent [19]
Bacchetti et al.

[11] Patent Number: 5,840,490
[45] Date of Patent: Nov. 24, 1998

[54] TELOMERASE ACTIVITY ASSOCIATED WITH HEMATOLOGICAL AND COLORECTAL MALIGNANCIES

[75] Inventors: Silvia Bacchetti; Christopher M. Counter; Brian Leber, all of Hamilton, Canada; Calvin Bruce Harley, Palo Alto, Calif.

[73] Assignee: McMaster University, Hamilton, Canada

[21] Appl. No.: 485,454

[22] Filed: Jun. 7, 1995

[51] Int. Cl.[6] .............................. C12Q 1/68; C12Q 1/70; C12P 19/34; C07H 21/02
[52] U.S. Cl. ................................. 435/6; 435/5; 435/911; 435/912; 536/24.3; 536/24.31; 536/24.32; 536/24.33
[58] Field of Search .................................. 435/5, 183, 6, 435/184, 91.1, 194, 91.2; 536/24.3, 24.31, 24.33

[56] References Cited

U.S. PATENT DOCUMENTS

| | | |
|---|---|---|
| 4,683,202 | 7/1987 | Mullis ....................................... 435/91 |
| 5,489,508 | 2/1996 | West et al. .................................. 435/6 |
| 5,629,154 | 5/1997 | Kim et al. ................................... 435/6 |
| 5,636,613 | 6/1997 | Shay et al. .................................. 435/6 |
| 5,645,986 | 7/1997 | West et al. .................................. 435/6 |
| 5,648,215 | 7/1997 | West et al. .................................. 435/6 |

FOREIGN PATENT DOCUMENTS

WO 93/23572  11/1993  WIPO .
WO 95/13381   5/1995  WIPO .

OTHER PUBLICATIONS

Adamson et al., Significant Telomere Shortening in Childhood Leukemia, Cancer Genet Cytogenet, 61:204–206 (1992).
Blackburn et al., Recognition and Elongation of Telomeres by Telomerase, Genome, 31:553–560 (1989).
Blackburn, Structure and Function of Telomeres, Nature, 350:569–573 (May 1991).
Counter et al., Telomere Length and Telomerase Activity Hematological Malignancies, Proceeding of the American Association for Cancer Research, 36:555, Abstract No. 3308 (Mar. 1995).
Counter et al., Stabilization of Short Telomeres and Telomerase Activity Accompany Immortilization of Epstein–Barr Virus–Transformed Human B Lymphocytes, J. Virology, 68(5):3410–3414 (May 1994).
Counter et al., Telomerase Activity in Normal Leukocytes and in Hematologic Malignancies, Blood, 85(9):2315–2320 (May 1995).
Counter et al., Telomeras Activity in Human Ovarian Carcinoma, Proc. Natl. Acad. Sci., 91:2900–2904 (Apr. 1994).
Counter et al., Telomere Shortening Associated with Chromosome Instability is Arrested in Immortal Cells Which Express Telomerase Activity, The EMBO Journal, 11 (5):1921–1929 (May 1992).

Greider and Blackburn, The Telomere Terminal Transferase of Tetrahymena Is a Ribonucleoprotein Enzyme with Two Kinds of Primer Specificity, Cell, 51:887–898 (1987).
Greider and Blackburn, A Telomeric Sequence in the RNA of Tetrahymena Telomerase Required for Telomere Repeat Synthesis, Nature, 337:331–337 (1989).
Greider, Telomerase Is Processive, Molecular and Cellular Biology, 11:4572–4580 (Sep. 1991).
Guerrini et al., Subtelomeric as Well as Telomeric Sequences are Lost from Chromosomes in Proliferating B Lymphoctes, Human Molecular Genetics, 2(4):455–460 (1993).
Harley et al., Telomeres Shorten During Ageing of Human Fibroblasts, Nature, 345:458–460 (May 1990).
Harley, Telomere Loss: Mitotic Clock or Genetic Time Bomb?, Mutation Research, 256:271–282 (1991).
Hastie et al., Telomere Reduction in Human Colorectal Carcinoma and with Ageing, Nature, 356:866–868 (Aug. 1990).
Hiyama et al., Correlating Telomerase Activity Levels with Human Neuroblastomas Outcomes; Nature Medicine, 1(3):249–255 (Mar. 1995).
Hiyama et al., Length of Telomeric Repeats in Neuroblastoma: Correlation with Prognosis and Other Biological Characteristics, Jpn. J. Cancer Res., 83:159–164 (1992).
Kim et al., Specific Association of Human Telomerase Activity with Immortal Cells and Cancer, Science, 266:2011–2015 (Dec. 1994).
Klingelhutz et al., Restoration of Telomeres in Human Papillomavirus–Immortalized human Anogential Epithelial Cells, Moleular and Cellular Biology 14(2):961–969 (Feb. 1994).
Nilsson et al., Telomerase Activity in vivo in Human Malignant Hematopoietic Cells, Oncogene, 9:3043–3048 (1994).
Ohyashiki et al., Telomere Shortening in Leukemic Cells is Related to Their Genetic Alterations but not Replicative Capability, Cancer Genet Cytoogenet, 78:64–67 (1994).
Shay et al., E6 of Human Papillomavirus Type 16 Can Overcome the M1 Stage of Immortalization in Human Mammary Epithelial Cells but not in Human Fibroblasts, Oncogene, 8:1407–1413 (1993).
Shay et al., Loss of Telomeric DNA During Aging May Predispose Cells to Cancer, International Journal of Oncology, 3:559–563 (1993).

(List continued on next page.)

Primary Examiner—W. Gary Jones
Assistant Examiner—Jeffrey Fredman
Attorney, Agent, or Firm—Melya J. Hughes; Richard L. Neeley; Kevin R. Kaster

[57] ABSTRACT

Methods for detecting hematologic and colorectal malignancies are provided comprising: (a) collecting a sample suspected of containing cancer cells; (b) analyzing the sample for telomerase activity; (c) correlating the presence of telomerase activity with the presence of cancer cells. A method for staging leukemia is also provided comprising analyzing a blood or bone marrow sample for telomerase activity, correlating the activity with a standard level of telomerase activity, and correlating a low telomerase activity with early stage leukemia.

19 Claims, No Drawings

OTHER PUBLICATIONS

Windle and McGuire, Telomeres: The Long and the Short of It, Proceedings of the American Association for Cancer Research, Eighty–Third Annual Meeting of the American Association for Cancer Research, 33:594–595 (Mar. 1992).

Yamada et al, Telomeric DNA in Normal and Leukemic Blood Cells, *J. Clin. Invest.*, 95:1117–1123 (Mar. 1995).

Chadeneau et al, "Telomerase activity in normal and malignant murine tissues", Oncogene 11:893–898, 1995.

TELOMERASE ACTIVITY ASSOCIATED WITH HEMATOLOGICAL AND COLORECTAL MALIGNANCIES

TECHNICAL FIELD

The present invention relates to telomerase, a ribonucleoprotein enzyme involved in telomere DNA synthesis, and provides methods for relating telomerase activity with hematological and colorectal malignancies. The invention provides methods and compositions relating to the fields of molecular biology, chemistry, pharmacology, and medical diagnostic and prognostic technology.

BACKGROUND

Telomeres are specialized structures at the ends of eukaryotic chromosomes and are composed of DNA consisting of simple repetitive G-rich sequences (TTAGGG in vertebrates) associated with specific proteins (Meyne et al, 1989, *Proc. Natl. Acad. Sci. USA* 86:7049–7053). Telomeres are essential for chromosome stabilization, protecting them from illegitimate recombination and degradation (Blackburn, 1991, *Nature* 350:569–573) and providing a buffer against loss of terminal sequences due to the inability of DNA polymerase to fully replicate the ends of a linear DNA template (Olovnikov, Doklady, 1971, *Biochem.* 201:394; Watson, 1972, *Nat. New Biol.* 239:197–201; Olovnikov, 1963, *J. Theor. Biol.* 41:181–190). In all normal somatic cells examined to date, telomeres shorten with each cell division. This progressive loss of telomeric DNA has been proposed to be the mitotic clock by which the number of divisions of a normal cell is regulated (Harley et al., 1992, *Exp. Gerontol.* 27:375). A sufficiently short telomere(s) may be the signal for replicative senescence in normal somatic cells, either in culture or with aging cells in Vivo (Harley, 1991, *Mut. Res.* 256:271–282; Harley et al. (1992); Hayflick L., 1965, *Exp. Cell Res.* 37:614–636). In vitro transformation confers an extended lifespan to cells that continue to lose telomeric DNA, but these eventually undergo proliferative crisis accompanied by cell death with the exception of rare immortal clones that emerge (Counter et al., 1992, *EMBO* 11:1921–1929; Counter et al., 1994a, *J. Virol.* 68:3410–3414; Shay et al., 1993, *Oncogene* 8:1407; Guerrini et al., 1993, *Hum. Mol. Genet.* 2:455; Klingelhutz et al, 1994, *Mol. Cell. Biol.* 14:961; Girardi et al. 1969, *Intl. J. Natl. Cancer Inst.* 42:867–874). These immortal cells emerging from crisis have short telomeres (Counter et al., 1992, 1994a; Shay et al., 1993; Klingelhutz et al., 1994). At proliferative crisis, telomeres are shortened to the point that they may no longer stabilize chromosome ends, and the ensuing genomic instability may contribute to the observed cell deaths (Counter et al, 1992, 1994a). In contrast, the vast majority of immortal cells examined to date shows no net loss of telomere length or sequence with cell divisions, suggesting that maintenance of telomeres is required for cells to escape from replicative senescence and to proliferate indefinitely (Counter et al, 1992; Counter et al., 1994, *Proc. Natl. Acad. Sci. USA* 91:2900–2940). The acquisition of extended proliferative capacity, and even of immortality, has also been suggested to occur in vivo during tumorogensis (Stamps et al., 1992, *Eur. J. Cancer* 28A: 1495).

Telomeric DNA is synthesized de novo by telomerase (Greider et al., 1985, *Cell* 43:405–413; Blackburn, 1992, *Ann. Rev. Biochem.* 61:113–129), a unique ribonucleoprotein DNA polymerase, using as a template a sequence contained within the RNA component of the enzyme (Greider and Blackburn, 1985, *Cell* 43:405–413; Greider and Blackburn, 1989, *Nature* 337:331–337; Yu et al, 1990, *Nature* 344:126–132; Blackburn, 1992). Methods for detecting telomerase activity, as well as for identifying compounds that regulate or affect telomerase activity, together with methods for therapy or diagnosis of cellular senescence and immortalization by controlling or measuring telomere length and telomerase activity, have also been described (PCT patent publication No. 93/23572, published Nov. 25, 1993; Kim et al., 1994, *Science* 266:2011–2014). Other methods for assaying telomerase activity in cell samples rely on the incorporation of radioactively labelled nucleotides into a telomerase substrate (Morin, 1989, *Cell* 59:521–529). The conventional assay uses an oligonucleotide substrate, a radioactive deoxyribonucleotide triphosphate (dNTP) for labelling, and gel electrophoresis for resolution and display of products. Because telomerase stalls and can release the DNA after adding the first G in the 5'-TTAGGG-3' telomeric repeat, the characteristic pattern of products on the gel is a six nucleotide ladder of extended oligonucleotide substrates. The phase of the repeats depends on the 3'-end sequence of the substrate; telomerase recognizes where the end is in the repeat and synthesizes accordingly to yield contiguous repeat sequences. Although telomeric sequence oligonucleotides are efficient in vitro substrates, telomerase will also synthesize repeats using substrates comprising non-telomeric DNA sequences.

Using such methods, scientists have analyzed various human cells and tissues for the presence of telomerase activity. Telomerase activity has not been detected at biologically significant levels (that level required to maintain telomere length over many cell divisions) in normal non-germline tissues or transformed but pre-immortal human cells, where telomere shortening occurs. However, telomere stabilization (Counter et al., 1992, 1994a; Shay et al., 1993), or even elongation (Klingelhutz et al.,1994), occurs concomitant with detection of telomerase activity in cells immortalized in vitro suggesting that telomerase activity and maintenance of functional telomeres are essential for indefinite cell proliferation (Counter et al., 1992, *EMBO J.* 11:1921–1929; Kim et al., 1994, *Science* 266:2011–2015; Counter et al., 1992, 1994a, Blackburn, 1994, *Cell* 77:621). Telomerase activity has also been detected in a variety of human tumors and of tumor-derived cell lines (Counter et al, 1994b, *Proc. Natl. Acad. Sci. USA* 91: 2900–2904; Counter et al., 1995, *Blood* 9:23 15–2320; Kim et al., 1994; Nilsson et al., 1994, *Oncogene* 9:3043–3048) suggesting that telomerase activity is required for cell immortality in vitro and in vivo, and that the enzyme may represent a prevalent tumor marker. For example, telomerase activity has been demonstrated to be present in metastatic ovarian carcinoma and short telomeres to be stabilized in vivo (Counter et al., 1994b). Enzymatic activity has also been analyzed in other advanced malignancies, including those of the hematopoietic lineage (Kim et al, 1994; Nilsson et al., 1994). Specifically, Kim et al. (1994) have detected telomerase activity in late stage chronic lymphoid leukemia (CLL) and in acute lymphoid leukemia (ALL) samples, whereas Nilsson et al. (1994) reported no activity in acute myeloid leukemia (AML) samples. The presence of short telomeres, despite detectable telomerase activity and the fact that complete loss of telomeric DNA entails a substantial number of cell divisions, suggest that selection for telomerase activation is likely to be a relatively late event in carcinogenesis (Counter et al, 1994b).

Cancer progression is generally unpredictable, cancer diagnosis providing little guidance as to whether the cancer will progress gradually or aggressively in an individual. As an example, chronic lymphoid leukemia (CLL) is initially characterized by a very slow accumulation of terminally differentiated B lymphocytes, whose number may double in as long as 5 years. The disease becomes gradually more aggressive but rarely undergoes blast transformation (Vincent, 1990, *Gunz's Leukemia,* 5th edition, Eds: William Dameshek and Fredrick, WB Saunders Company, Toronto, Canada, 1990; Rai, *Hematology-basic principles and practice Eds*: Hoffman et al., Churchill Livingstone, N.Y. On the other hand, acute myeloid leukemia (AML) is a highly aggressive disease resulting from aberrant proliferation and maturation of progenitor stem cells (Vincent, 1990; Lowenberg et al., 1991, *Hematology-basic principles and practice,* Eds: Hoffman et al., Churchill Livingston, N.Y.). Myelodysplastic syndrome (MDS), a neoplasia of the bone marrow characterized by variable, but often high, proliferation rates, can progress through a variety of stages and convert to AML (Tricot, *Hematology-basic principles and practice,* 1991, Eds: Hoffman et al, Churchill Livingston, N.Y.; Mayer et al., 1990, *Gunz's Leukemia;* 5th edition, WB Saunders Company, Toronto, Canada) and can therefore be considered a pre-AML condition. Recent observations on terminal restriction fragment (TRF) length (Ohyashiki et al., 1994, *Cancer Res.* 54:3557) identified three classes of MDS patients those with i) short TRFs at diagnosis and no change during disease evolution; ii) large TRFs decreasing in length as the disease evolved; or iii) large and stable TRFs. Thus, TRF length does not provide a method for staging MDS. Similarly, prognostic methods exist for AML, but have either given variable results or require sophisticated equipment (Vidriales et al, 1995, *British J. of Hematology,* 89: 342–348). Terminal restriction fragments (TRFs) of variable length relative to normal colorectal mucosa have also been detected in adenocarcinoma (Hastie et al., 1990, *Nature:* 346:866–868; Hiyama et al., 1995, *Int. J. Oncology* 6:13–16), with shorter TRFs in adenomatous polyps (Hastie et al., 1990) than in isogeneic normal tissue, comparable to results obtained with the tumor. Thus TRF does not provide a method of detecting colorectal malignancies. There remains a need for simple diagnostic methods that enable a physician to detect malignancies with greater accuracy and to differentiate aggressive cancers from less aggressive cancers, and to assess whether treatment of cancers in a patient by surgery, chemotherapy, or other means is required, and this invention meets that need.

SUMMARY OF THE INVENTION

The present invention provides diagnostic methods for detecting cancerous cells. The basic method involves the following steps: (a) collecting a sample suspected of containing cancerous cells; (b) analyzing said sample for telomerase activity; (c) correlating said activity with a standard level of telomerase activity; and (d) correlating a high telomerase activity with the presence of cancerous cells. The standard level can be a predetermined level obtained from assaying cells known to have no or low telomerase activity. The method is useful for diagnosing any cancer, and is illustrated below with reference to, leukemia, in particular, acute myeloid leukemia (AML) and chronic lymphoid leukemia (CLL), and colorectal cancer. Thus, the method can be performed using samples such as bone marrow or blood samples for leukemia diagnosis, and cells obtained from colon or rectal biopsies for colorectal cancer diagnosis.

In a further aspect of the invention, diagnostic methods are provided for differentiating between early stage leukemias and late stage leukemias based on assaying telomerase activity. The method involves the steps of: (a) collecting a blood or bone marrow sample from an individual suspected of having leukemia; (b) analyzing said sample for telomerase activity; (c) correlating said activity with a standard level of telomerase activity; and (d) correlating a low telomerase activity with early stage leukemia and a high telomerase activity with late stage leukemia. The standard level can be determined from a range of telomerase levels known to be associated with the different clinical outcomes of leukemic progression. The method is used to assess the extent of progression of leukemia in an individual and thus is useful in allowing a physician to make a prognosis of early stage and late stage leukemia, which can then be treated accordingly, as is described in more detail below.

DETAILED DESCRIPTION AND PREFERRED EMBODIMENTS

The present invention provides methods that allow for the detection and staging of colorectal and hematological malignancies, in particular chronic lymphoid leukemia and acute myeloid leukemia. In one aspect of the invention, a method is provided for detecting telomerase activity in a colorectal cell or tissue sample and relating the presence of telomerase activity to the presence of malignant cancer cells. In a further aspect of the invention, a method is provided that entails detecting telomerase activity in a blood, lymph node or bone marrow sample and relating the presence of elevated telomerase activity to the presence of leukemic cells. In yet another aspect of the invention, a method is provided that entails determining the level of telomerase activity in a cell or tissue sample and correlating the level obtained with early stage or late stage leukemia. The methods of the present invention will typically involve the detection of telomerase activity in a human cell or tissue sample, but one can also readily understand that samples tested by the present method can be obtained from agriculturally important mammals, such as cattle, horses, sheep, etc., or other animals of veterinary interest, such as cats and dogs. The assay is carried out on various cell or tissue samples, depending on the cancerous condition under examination. Typically, blood or bone marrow samples will be used for diagnosing leukemia, whereas intestinal mucosa, in particular colorectal biopsies or stool samples will be used for diagnosing colorectal cancer. The sample can be freshly isolated or stored frozen (after flash freezing in liquid nitrogen) until use. A "sample" is the material being analyzed which is usually subjected to pretreatment to provide the telomerase in assayable form. This would normally entail forming a cell extract, methods for which are known in the art (for example, see Scopes, 1987, *Protein Purification: Principles and Practice,* Second Edition, Springer-Verlag, New York). Preferably the detergent-based extraction protocol described below is used.

In the broader aspects of the invention, there is no limitation on the collection and handling of samples as long as consistency is maintained. Consistency of measurement of telomerase activity in clinical samples can be ensured by using a variety of techniques. For example, to control for the quality of each tissue extract, another enzymatic activity, such as alkaline phosphatase, can serve as an internal control. In addition, an internal standard can be measured concurrently with telomerase in the sample as a control for assay conditions.

The level of telomerase can be determined by detecting the telomerase ribonucleoprotein or any component thereof using methods known in the art. For example, telomerase can be detected by immunoassays using antibodies specific for telomerase. Methods for preparing antibodies and suitable immunoassays are described in *Antibodies: A Labora-* tory Manual, 1988, Eds: Harlow and Lane, Cold Spring Harbor, N.Y. The antibody can be used, for example, in Western blots of two dimensional gels where the protein is identified by enzyme linked immunoassay or in dot blot (Antibody Sandwich) assays of total cellular protein, or partially purified protein. Methods for sample concentration and protein purification are described in the literature (see Scopes, 1987). For example, if desired, the telomerase present in the cell extract can be concentrated, by precipitating with ammonium sulfate or by passing the extract through a commercially available protein concentration filter, e.g., an Amicon or Millipore ultrafiltration unit. The extract can be applied to a suitable purification matrix, such as an anion or a cation exchange resin, or a gel filtration matrix, or subjected to preparative gel electrophoresis. In such cases, the telomerase and protein yield after each purification step needs to be considered in determining the level of telomerase in a sample.

Preferably, telomerase activity is measured. If desired (but not required), the telomerase can undergo further manipulations after formation of the cell extract for activity assays, as described above. However, these separations are generally difficult and may result in loss of telomerase activity, and thus, because the assay does not require purified telomerase, cell extracts that have not been pretreated are preferred for the assay.

In this invention, there are no limitations on the type of assay used to measure telomerase activity. Any of the current assays for telomerase activity can be used, as well as assays that may be developed in the future. A preferred method involves the preparation of a cell extract using a detergent lysis method and the analysis of telomerase activity described in detail in the Examples section below by extension of a nucleic acid substrate by telomerase and replication of extended substrates in a primer extension reaction, such as the polymerase chain reaction (PCR).

The Telomeric Repeat Amplification Protocol (TRAP assay) (Kim et al, 1994) is particularly well suited for providing a variety of means to quantitate the amount of telomerase in a sample. One important means for obtaining quantitative information is the use of a control oligonucleotide template added to each reaction mixture in a known amount. An illustrative control oligonucleotide comprises, in 5'-3' order, a telomerase substrate sequence, a spacer sequence (which can be any sequence of nucleotides or length and can alter spacing of the ladder produced by electrophoresis of reaction products produced from telomerase containing samples), a telomeric repeat sequence (typically present in multiple, e.g., 2 to 50, copies), and a sequence complementary to the primer used in the assay (and so which may simply be a portion of the telomeric repeat sequence). Of course, an oligonucleotide complementary to the control sequence defined above can also serve as the control sequence, and a double-stranded control nucleic acid can also be employed.

Alternatively, one can add a control nucleic acid of any sequence to the reaction mixture in known amounts and amplify the control with primers which can be the same as or different from those used to amplify the extended telomerase substrate. The control oligonucleotide and/or the primers used to amplify the control oligonucleotide can be labelled identically to or differently from the label used to label the telomerase extension products. Use of an internal control not only facilitates the determination of whether the assay was conducted properly but also facilitates quantitation of the telomerase activity present in the sample.

While PCR provides for exponential accumulation of primer extension products, even linear accumulation of primer extension products can provide useful results. Thus, one can use a single primer and merely make many copies of a single strand of the duplex nucleic acid that is produced when PCR is employed. Moreover, such copies can be made by means other than polymerase-mediated primer extension. Suitable methods include the ligase chain reaction (Barany, 1991, Proc. Natl. Acad. Sci. USA 88:189–193), nucleic acid sequence-based amplification (Compton, 1991, Nature 350:91–92), self-sustained sequence replication (Guatelli et al, 1990, Proc. Natl. Acad. Sci. USA 87:1874–1878), strand displacement amplification (Walker et al., 1992, Proc. Natl. Acad. Sci. USA 89:392–396), and branched DNA signal amplification (Urdea, 12 Sep. 1994, Bio/Tech. 12:926–928; U.S. Pat. No. 5,124,246), although the latter method involves amplification of the signal produced upon probe hybridization to a target nucleic acid. As one example, DNA ligase can be used to ligate together two oligonucleotides hybridized to a template nucleic acid. If, as in PCR, the duplex nucleic acid is then denatured, then one can repeat the process of ligation and denaturation many times to accumulate many complementary copies of the original template, i.e., the extended telomerase substrate. If one additionally adds two other oligonucleotides complementary to the copy produced by ligation of the first two oligonucleotides on the extended telomerase substrate and selects those oligonucleotides such that DNA ligase can ligate the two together to form a copy of the original extended telomerase substrate, then one has the basic components of an LCR.

To illustrate, one could employ LCR to amplify an extension product of a telomerase substrate to detect telomerase activity in a sample using the following 4 oligonucleotide "ligomers":

LTS (5'-CCCAATCCGTCGAGCAGAGTTAG-3') (SEQ ID NO:1),

CLT (5'-TAACTCTGCTCGACGGATTCCC-3') (SEQ ID NO:2),

LC (5'-GGGTAACCCTAACCCTAACCC-3') (SEQ ID NO:3), and

LG (5'-GGTTAGGGTTAGGGTTAAA-3') (SEQ ID NO:4). The LC and CLT ligomers will anneal to an extended telomerase substrate and then be ligated with DNA ligase to form a template for ligation of the LTS and LG ligomers. These ligomers have been selected so that no two ligomers can anneal to form a duplex nucleic acid that can be joined to another duplex nucleic acid in the mixture by the blunt-end ligation activity of DNA ligase. A wide variety of such ligomers can be used in the method to minimize template-independent product formation. LCR amplification of telomerase extension products produces an amplified product of uniform size and so is conducive to quantitative analysis.

Moreover, a variety of different types of oligonucleotides can be used in telomerase activity assays. While the discussion above and Examples below illustrate assay methods with results obtained using oligodeoxyribonucleotide telomerase substrates and primers with DNA polymerase, the activity assay used in the present invention is not so limited. Thus, one can employ oligoribonucleotides or oligonucleotides that comprise one or more modified (i.e., synthetic or non-naturally occurring) nucleotides in the telomerase assay. In similar fashion, one can employ an RNA polymerase to extend a primer or to copy an extended telomerase substrate. These and other variations of the present method will be apparent to those of skill in the art upon consideration of this description of the invention.

In the diagnostic methods of the invention, the assay will be conducted to determine telomerase activity present in a sample. Generally, any detectable level of telomerase activity is considered elevated in cells from normal, post-natal human somatic tissue other that hematopoietic or other stem cells. Thus, for colorectal cancer, any telomerase activity above zero is considered to be elevated, whereas for leukemia any telomerase activity above that of a control blood or bone marrow sample from a normal donor is considered to be elevated. In one aspect of the invention, the level of telomerase activity is determined for a sample to determine whether the sample has low or high activity. The terms "low telomerase activity" and "high telomerase activity" relate to the relative levels of telomerase activities found in cancers of different clinical stages. To assess the clinical stage of cancer, the level of telomerase in the cell extract is correlated to a standard value of telomerase activity, which is selected to divide a population of patients into two statistically significant classes, for example, those in the early stages of leukemia and those in the late stages of leukemia. The method can thus be applied to chronic lymphoid leukemia or to acute myeloid leukemia, where myelodysplastic syndrome is considered to be an early stage of acute myeloid leukemia. In one embodiment of the invention, the standard value is selected to be the level of telomerase found in a sample known to have low telomerase activity. For example, as is described in the Examples section below, the level of telomerase activity found in normal blood samples is comparable to that observed in late stage chronic lymphoid leukemia. Thus, the level of telomerase of a normal blood sample can be chosen as the standard value for chronic lymphoid leukemia and activity can be correlated to late stage CLL. Furthermore, the level of telomerase activity found in normal bone marrow is below that of MDS which is below that of AML. Thus, telomerase activity at a level greater than that found in normal bone marrow is considered to be indicative of a myeloid leukemic condition but does not alone allow staging of the condition. A second standard value is therefore required for a physician to differentiate between MDS and AML.

In this case, the second standard level of telomerase activity is determined by collecting data to obtain a statistically significant correlation of telomerase levels with the different leukemic stages. It will be apparent to one of skill in the art in light of the present specification that this method of determining the standard value can also be applied to determining other standard values, e.g., that dividing a population into catagories of non-cancerous and cancerous conditions. Relative levels can be determined by various methods that involve measurement of telomerase activity in aliquots of a sample under different conditions and include, but are not limited to, serial dilution of the sample, incubating sample aliquots over incrementing time periods, etc. These conditions are chosen to detect both high and low telomerase activity in at least one sample aliquot. For example, the activity assay can be carried out for a length of time sufficient to detect low telomerase activity in at least one aliquot, whereas shorter incubation times would result in detection of only high telomerase activity. Similarly, a sufficient amount of extract can be used in the activity assay to detect low telomerase activity in at least one aliquot, whereas with lesser amounts of cell or tissue extract, only high telomerase activity would be detectable. The amount of extract added can be standardized by determining the protein concentration of the extract, as is known in the art. The methods described in the Examples section below illustrate serial dilution of an extract to establish the linear range of enzyme activity for the purpose of quantitation. The total counts resulting from the reaction products are then determined and normalized to total protein content in a sample, thus allowing estimation of relative telomerase levels in different samples. Typically, a "low telomerase activity" would be at least 2-fold, preferably at least 4-fold, more preferably at least 6-fold, more preferably at least 8-fold times less than a "high telomerase activity" under comparable conditions of measurement. One of ordinary skill in the art recognizes that if a less sensitive assay is chosen to determine the level of telomerase in a sample, it may be necessary to increase the amount of extract used or to pretreat the extract using routine methods as described above to provide detectable levels of telomerase. The assay methods do not necessarily require measurement of absolute values of telomerase, unless it is so desired, because relative values are sufficient for the methods of the present invention; however, any known method for quantitating telomerase or telomerase activity could be used for this determination.

A predetermined range of telomerase activity is established for the same cell or tissue sample obtained from subjects having known clinical outcomes by analyzing telomerase activity in aliquots of the same sample under different conditions, where such conditions allow the measurement of relative levels of telomerase activity as described above. In addition, the clinical staging of the leukemic patient from which the sample was taken is related to the measured level of telomerase activity. Sufficient measurements are made to produce a statistically significant range of values for the value to which a comparison will be made. The predetermined range of telomerase activity is typically obtained by using the same assay technique that will be used in the application of the method to an individual being tested to ensure the highest correlation. Standard values may vary with the specific cell or tissue extract for which telomerase activity is measured and with the specific assay used. The predetermined range of telomerase activity for a given cell or tissue sample can then be used to determine a standard value above which a level of telomerase activity would be considered high activity and correlated to late stage leukemia. The method of the invention does not require the measurement of any other substance or, in this latter described aspect of the invention, can even be dependent upon a single measurement, once a standard level for an assay procedure is established. In this case, the assay is carried out on a sample under conditions that would only detect telomerase activity above the standard level or would quantitate the telomerase level.

A measured high level of telomerase activity relative to the standard value (e.g., detectable activity in more dilute samples, detectable activity in samples incubated for shorter lengths of time, etc.) is an indication of late stage leukemia, suggesting that the physician should employ an aggressive therapy. A measured low telomerase activity relative to the standard level or a telomerase activity equal to the standard level is an indication of early stage leukemia with the provisos that in early myeloid leukemia (i.e. MDS) the low telomerase activity exceeds the telomerase levels present in normal bone marrow samples, and in early CLL, the low telomerase activity is below that of normal blood samples. The criteria for clinical staging of cancers are known in the art and provides an indication of survival potential of an individual.

Those of skill in the art will also recognize that, while the use of cell extracts is preferred for most purposes, one can also modify the method so that intact cells can be employed. In this embodiment, one treats intact cells with the telomerase substrate oligonucleotide, following which the oligonucleotide will be extended if the cell possesses functional telomerase activity. Established in situ PCR or LCR technology with a polymerase or ligase, a primer, and nucleoside triphosphates (if a polymerase is employed) is then used on fixed cells to amplify telomerase-extended substrate oligonucleotides. Telomerase positive cells can then be detected by microscopy, utilizing, e.g., incorporation of a labelled nucleotide or oligonucleotide during primer extension. These methods are easily modified to give quantifiable data as is described above.

The method of the present invention allows the detection of colorectal and leukemic conditions and allows the staging of a leukemic condition by detecting the level of telomerase activity in cancer cells, thus allowing physicians to administer an appropriate therapy. This determination of telomerase activity in a cell or tissue extract gives a physician early warning of the prognosis, even in the absence of clinical symptoms so that clinical symptoms can be closely monitored and patient treatment modified (e.g., by implementing aggressive treatment, e.g., surgery, radiation therapy, and/or chemotherapy). Assays for a given analyte, including this assay for telomerase activity, are not expected to be obtained or to be interpreted by an attending physician in the absence of additional information. Although the present method for testing the level of telomerase activity provides much useful information regarding the progression of a disease, tests that may provide additional information in conjunction with the present method include diagnostic tests for DNA ploidy, fraction of cells in S-phase, nodal status, p53, p16, p21, ras, and other oncogenes. Additionally, the results of any assay are best considered to be indicative of the probability of a presence of a clinical condition rather than as absolute proof. The same situation exists for the present invention. Nevertheless, an indication of colorectal or leukemic diagnosis and prognosis is clinically useful information and can be used by a skilled medical practitioner in combination with other information to care for patients in a more informed manner than would be possible if the information were not available. In particular, a physician can determine whether additional diagnostic tests quantitating telomerase activity should be required periodically to follow leukemic progression and the effect of therapy thereon. The methods of the invention are useful in determining the most effective therapy in the case of early stage and late stage prognosis, and even preventing unnecessary therapy that could result in harmful side-effects. Thus, the present invention can be used for prognosis of any of a wide variety of leukemias including without limitation: B-cell, mixed-cell, null-cell, T-10 cell, T-cell chronic, HTLV-II-associated, lymphocytic acute, lymphocytic chronic, mast-cell, and myeloid leukemias.

Preferred methods of the invention allow for staging of CLL and AML. As described in the Examples below, unlike other somatic tissues, peripheral, cord blood and bone marrow leucocytes from normal donors expressed low levels of telomerase activity. Leucocytes from chronic lymphocytic leukemia (CLL) patients were demonstrated to have lower activity in early disease than controls and elevated levels in late disease relative to early disease. Early stage CLL is frequently asymptomatic; thus assays for its early diagnosis are particularly valuable. Relative to bone marrow controls, telomerase activity was enhanced in myelodysplastic syndrome (MDS) and more significantly so in acute myeloid leukemia (AML). Regardless of telomerase levels, telomeres shortened with progression of the diseases. In a further aspect of the invention, detectable telomerase activity was shown to correlate with acquisition of malignancy in colorectal cancer. Telomerase activity was not detected in 21 benign adenomatous polyps from 15 patients, consistent with lack of the enzyme in the benign stage.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al, 1989, *Molecular Cloning: A Laboratory Manual*, Second Edition; *DNA Cloning*, 1985, Volumes I and II Ed: D. N. Glover); Scopes, *Protein Purification: Principles and Practice,* 1987, Second Edition Springer-Verlag, New York; and *Handbook of Experimental Immunology,* 1986, Volumes I–IV Eds: D. M. Weir and C. C. Blackwell.

The present invention also provides kits for performing the methods of the invention. Such kits can be prepared from readily available materials and reagents and can come in a variety of embodiments. For example, such kits can comprise any one or more of the following materials: reaction tubes, buffers, detergent, oligonucleotide telomerase substrates, control reagents, oligonucleotide primers, and instructions. A wide variety of kits and components can be prepared according to the present invention, depending upon the intended user of the kit and the particular needs of the user.

The following examples describe specific aspects of the invention to illustrate the invention and provide a description of the methods for those of skill in the art. The examples should not be construed as limiting the invention, as the examples merely provide specific methodology useful in understanding and practice of the invention.

EXAMPLES

Example 1

Detection of Telomerase Activity in Normal Leucocytes and in Hematological Malignancies Extracts from samples obtained from blood or bone marrow of cancer patients or normal donors were analyzed for telomerase activity using a PCR-based assay called the "TRAP" assay (<u>T</u>elomeric <u>R</u>epeat <u>A</u>mplification <u>P</u>rotocol). Leucocytes from patients with early (O–II) and late (III–IV) stage CLL, with MDS and with AML were assayed for enzyme activity. As controls, leucocytes from cord, peripheral blood and bone marrow of normal donors were used. A telomerase positive extract elongates a single stranded primer by addition of $T_2AG_3$ repeats and the elongated products are amplified in the PCR step (Kim et al. (1994)). Pretreatment of the extract with RNase will abolish telomerase activity by degrading the templating RNA of the enzyme (Blackburn, (1992)).

Isolation and Culturing of Cells

Normal human skin fibroblasts were cultured in α-MEM, supplemented with 10% fetal calf serum (FCS), 293 CSH cells (Stillman et al., 1985, *Mol. Cell. Biol.* 5:2051) were cultured in Joklik medium supplemented with 5% FCS, and B4 cells, an immortal line derived from EBV-infected human B lymphocytes (Counter et al., 1994), were grown in RPMI with 10% FCS serum. Samples were obtained with informed consent from normal donors or from cancer patients at diagnosis or during follow-up. The age of normal adult donors ranged from 25 to 55 years and that of patients from 40 to 80 years, without significant differences in the average age between groups. Chronic lymphoid leukemia was staged according to Rai, (1991) and samples were obtained from blood, when white blood cell counts exceeded $15 \times 10^9$/L. Myelodysplastic syndrome samples were isolated from bone marrow while normal and acute myeloid leukemia samples came from both sources. All samples were processed immediately after collection without expansion in culture. Following two washes in phosphate buffered saline (PBS), low density mononuclear cells were isolated by Ficoll-Hypaque density gradient centrifugation and assayed.

Preparation of Cell Extracts

Most S100 extracts were prepared from $10^7$ cells using the hypotonic-detergent lysis method (Counter et al., 1994a), with the exception that the lysis buffer contained 0.5% CHAPSO instead of 0.5% Nonidet P-40 (Kim et al, 1994). A few extracts were prepared from $10^8$ cells using a hypotonic-Dounce homogenization method (Counter et al., 1992). Control extracts were treated with RNase to a final concentration of 0.02 μgl for 10 min at 21° C.

Analysis of TRF lengths of normal and leukemic cells

TRFs are comprised of telomeric and subtelomeric DNA, and variability in the lengths of both components gives rise to their heterogeneous size (Blackburn, 1991). Genomic DNA was isolated from leucocytes from a normal individual (PBL), or from patients with early or late stage CLL, MDS and AML and digested with HinfI and RsaI to liberate the terminal restriction fragments (TRFs), as previously described (Counter et al., 1992). The digested DNA was resolved in 0.5% agarose gels, which were dried, hybridized with a $^{32}$P-labelled telomere specific probe, CCCTAACCCTAACCCTAA, (SEQ. ID NO:5) stringently washed, and exposed to Phosphorimager screens (Molecular Dynamics, Sunnyvale, Calif.) (Counter et al., 1992). A mean TRF length was calculated using the total counts between 21 and 2 kbp, determined using ImageQuant software (Molecular Dynamics) (Counter et al, 1992; Kim et al, 1994) and recorded for simplicity as TRF length. Samples obtained from the same patient at different times are denoted by numbers after the sample's code (see Table 1).

In early stage CLL, TRF length varied considerably among samples but on average was 7.9 kbp, (Table 1). There was no detectable loss of telomeric DNA in samples taken two years apart from patients CLL1 and CLL4, as expected if telomere shortening occurred at the same rate as in normal leucocytes (~40 bp/year; Vaziri et al., 1993, *Proc. Natl. Acad. Sci. USA* 91:9857). TRF lengths in late CLL were more homogeneous and much reduced, with an average size of 4.4 kbp. A similar trend was observed for the myeloid diseases (Table 1), with TRFs being longer and extremely variable in size in MDS patients (average=11.1 kbp), and consistently and significantly shorter in AML samples (average=4.7 kbp).

Telomerase Assay

Telomerase activity in samples of leucocytes from patients with early or late chronic lymphoid leukemia (10 μg protein per assay), from patients with MDS or AML (5 μg protein per assay), from peripheral blood (10, 5, and 2.5 μg) and bone marrow (1 μg) leucocytes from normal individuals, and in control 293 (1 μg) and B4 (1 μg) cell lines, were assayed at the indicated amounts of protein. Telomerase was assayed by incubating cell extracts for 10 min at 21° C. with 0.1 μg of TS oligonucleotide 5'-AATCCGTCGAGCAGAGTT-3' (SEQ ID NO:6) in 20 mM Tris-HCl pH 8.3, 1.5 mM MgCl$_2$, 63 mM KCl, 0.005% Tween 20, 1 mM EGTA, 50 μM each dNTP, 0.5 mM T4-gene 32 protein, 2 μCiα$^{32}$PdCTP (3000 Ci/mmol) and 2 U Taq polymerase in a total volume of 50 μl in a tube containing 0.1 μg of CX primer 5'-CCCTTACCCTTACCCTTACCCTAA-3' (SEQ ID NO:7) separated from the reaction by a wax barrier (Kim et al., 1994). Following elongation of the TS oligonucleotide by telomerase, products were PCR-amplified by 27 cycles at 94° C. for 30 seconds, 50° C. for 30 seconds and 72° C for 90 seconds. The first denaturation step inactivates telomerase and melts the wax barrier, releasing the CX primer for first strand synthesis. This protocol results in a 104 increase in sensitivity (Kim et al., 1994) compared to previous methods (Counter et al., 1992). Alternatively, the CX primer and Taq polymerase were added to reactions pre-warmed to 92° C. to reduce background. Polynucleotide kinase-labelling of the TS oligonucleotide, substitution of the CX primer with a primer unable to dimerize with TS (ACT: 5'-GCGCGGCTAACCCTAACCCTAACC-3') (SEQ ID NO:8), and the use of a standard for measuring PCR amplification (5'-AATCCGTCGAGCAGAGTTGGTTAGGGT-TAGGGTTAGGGTTAGGGTTAGGGTT AGGGTTAG-3'; SEQ ID NO:9), were also used to increase sensitivity and to provide better quantitation and comparison between assays. Results from all three assays were qualitatively consistent. Serial dilutions of S 100 extracts were assayed in triplicate to establish the linear range of enzyme activity for the purpose of quantitation. Reaction products were resolved in 15% non-denaturing polyacrylamide gels and exposed to Phosphor-Imager screens. Extracts were considered negative if no products were detected upon a 7 day exposure. Enzyme activity was expressed in arbitrary units as total counts of RNase-sensitive reaction products, determined using ImageQuant software, after normalization to total protein content. A minimum of two separate assays were used to determine the mean percentage activity of each sample except for CLL5, CLL9, MDS2, AML6 and AML7 for which a single assay was performed. The reaction products were shown to be RNase sensitive in a separate control assay where extracts had been pre-treated with RNase.

Assaying of samples from normal individuals revealed that telomerase was present in leucocytes from cord (3/3), peripheral blood (6/6), and bone marrow (4/4) (Table 1). Activity was low in all three tissues (on average ~0.8% that of the 293 cell line, and ~2% that of the B4 lymphocyte cell line) suggesting that enzyme expression may be limited to a small subset of normal leucocytes or may be insufficient for telomere maintenance, as supported by the observation that telomeres were significantly shorter in adult versus newborn leucocytes (Table 1). Leucocytes from early stage CLL patients (n=14) expressed on average lower telomerase activity than control samples (Table 1). In the vast majority (12/14 or 85%) activity was reduced on average by 70% (P=0.03), and only two cases exceeded control values. The latter samples (CLL19 and 20) were from patients with significant increase in white blood cell count and lymph nodes in the month prior to sampling. Conversely, in late stage CLL (n=7), four of the seven samples assayed (or 57%) had elevated enzyme levels compared to early stage samples (P=0.016), although cases with no or negligible activity persisted (Table 1). The average value for late CLL patients was comparable to that of normal blood. In the myeloid diseases (Table 1), MDS (n=6) and AML (n=7) samples had higher levels of telomerase activity on average than normal bone marrow, with a ~2-fold increase for MDS and a ~4-fold increase for AML (P=0.029). There was substantial variability in enzyme levels among samples suggesting variable activation of telomerase in MDS. However, a subgroup of MDS patients (4/6 or 67%) with significantly higher activity than controls (~3-fold on average) could be identified. Similarly, the majority (6/7 or 86%) of AML samples expressed on average ~5-fold more telomerase activity than normal bone marrow.

The results demonstrate that telomerase activity is present in leucocytes from bone marrow and peripheral blood from normal donors. However, despite the constitutive telomerase activity in normal tissues, the present inventors have detected distinct patterns of telomerase expression in samples from lymphoid and myeloid leukemias. In both diseases, leucocytes from early stage patients generally have less telomerase activity and longer TRFs than those from late stage patients. Samples not fitting either pattern, with short TRFs but low or no telomerase activity (CLL 3, 6, 10 and possibly AML 6) could represent populations in transition, although inability to detect enzyme activity for technical reasons cannot be excluded.

In the majority of early CLL, telomerase activity was undetectable or substantially reduced compared to control leucocytes suggesting that activity present in a subset of normal cells is diluted by the more numerous telomerase-negative CLL cells, resulting in reduced levels in the whole population. Although normal cells may also contribute to telomerase levels in MDS samples, in 4/6 of these cases enzyme levels were significantly elevated over control samples. Similar to our observations on late CLL, AML was associated with elevated telomerase activity relative to MDS. However, in the late stage of both leukemias, activity was substantially lower (at most ~16%) than that in a clonal population of immortalized B cells (Table 1), suggesting a preponderance of negative cells in the leukemic samples. CLL and AML differed with respect to levels of telomerase, with CLL samples being generally less active in accordance with the lower number of proliferating cells and/or the-higher degree of cell differentiation characteristic of CLL.

TABLE 1

| Sample | TRF* (kbp) | T'ase Activity† (% of B4 cells) | Sample | TRF* (kbp) | T'ase Activity (% of B4 cells) | Sample | TRF* (kbp) | T'ase Activity (% of B4 cells) |
|---|---|---|---|---|---|---|---|---|
| NORMAL BLOOD | | | EARLY STAGE CLL | | | LATE STAGE CLL | | |
| PBL1 | 13.3 | 3.3 | CLL1-1 | 8.1 | 0.5 | CLL6-2 | 3.8 | 0.5 |
| PBL2 | 12.7 | 1.5 | -2 | 8.0 | 0.7 | CLL9 | 6.0 | 1.3 |
| PBL3 | 11.6 | 1.3 | CLL2-1 | nd | 0 | CLL10 | 3.8 | 0 |
| PBl4 | 13.0 | 4.5 | -2 | 10.1 | 1.3 | CLL11 | 4.1 | 2.3 |
| PBL5 | 11.6 | 1.5 | CLL3-1 | 4.5 | 0 | CLL13-1 | 4.3 | na |
| PBL6 | 12.0 | 2.1 | -2 | 3.7 | 0.9 | -2 | 4.2 | 2.5 |
| mean: | 12.4 | | CLl4-1 | 8.4 | nd | CLL14 | 3.8 | 3.1 |
| | | | -2 | 11.4 | nd | CLL15 | 3.9 | na |
| CBL1 | 16.7 | 1.2 | CLL5 | 10.4 | 0.2 | CLL16 | 6.3 | na |
| CBL2 | 16.2 | 0.4 | CLL6-1 | 3.6 | na | CLL17 | 4.2 | na |
| CBL3 | 15.2 | 0.7 | CLL7 | 12.9 | 0.7 | CLL18 | nd | 4.3 |
| mean: | 16.0 | 1.8# | CLL8-1 | 8.4 | 0.2 | mean: | 4.4 | 2.0 |
| | | | -2 | nd | 1.4 | | | |
| | | | -3 | nd | 0.2 | | | |
| | | | CLL11 | S.S | 0.9 | | | |
| | | | CLL19 | nd | 2.3 | | | |
| | | | CLL20 | nd | 2.7 | | | |
| | | | mean: | 7.9 | 0.9 | | | |
| NORMAL BONE MARROW | | | MDS | | | AML | | |
| BM1 | nd | 0.6 | MDS1 | nd | 4.0 | AML1 | 4.4 | 5.9 |
| BM2 | 10.3 | 2.2 | MDS2 | 7.5 | 4.6 | AML2 | 4.8 | 12.0 |
| BM3 | 10.3 | 2.4 | MDS3 | nd | 1.1 | AML3 | 5.1 | 2.9 |
| BM4 | nd | 3.0 | MDS41 | 20.1 | 1.5 | Aml4 | 4.2 | 6.9 |
| mean: | 10.3 | 2.1 | -2 | nd | 7.6 | Aml5 | 6.5 | 14.3 |
| | | | MDS5 | 5.6 | 8.8 | AML6 | 4.3 | 1.9 |
| | | | mean: | 11.1 | 4.6 | AML7 | 3.6 | 18.1 |
| | | | | | | mean: | 4.7 | 8.9 |

Abbreviation: nd, not determined, na, not available
*The SD of TRF measurements ranged from 0 to 1.4 kbp, with an average of 0.3 kbp
†Activity of normal leukocytes from a peripheral (PBL), cord (CBL), bone marrow (BM), lymphoid and myeloid leukemic samples is expressed as % of B4 cells which have 40% the activity of 293 cells. The SD of telomerase activity of the normal tissues ranged from 0.4 to 4.2%, with an average of 1.5%. The SD of telomerase activity of the leukemic samples ranged from 0 to 5.5 with an average of 1.9.
Mean telomerase activity of PBL and CBL samples Example 2

Telomerase Activity Associated with Acquisition of Malignancy in Human Colorectal Cancer In this example, surgically excised samples from different grade colorectal tumors and control tissue were assayed for telomerase activity. The results demonstrate that telomerase activity is associated with acquisition of malignancy as it is detectable in colorectal carcinoma but not in adenomatous polyps.

Tissue samples were obtained at resection from 37 patients (Table 2) at the Mount Sinai Hospital (Toronto) or the Henderson Hospital (Hamilton). Five of these patients presented with inflammatory diseases (diverticular disease (DD), ulcerative colitis (UC) or Crohn's disease (CD)). The remainder were patients with Familial Adenomatous Polyposis (FAP, 10 individuals), sporadic colorectal polyps (1), colorectal adenocarcinoma (16), or liver metastases from previously resected colorectal adenocarcinoma (5). Samples from 3 of the FAP patients were obtained from duodenal periampullary polyps, a common extracolonic premalignant feature of the disease (Jagelman, *Oncology* 5: 23–27. 1991). The age of individuals ranged from 19 to 85 years with overlap between the ages of cancer and non-cancer patients (Table 2). Protein extracts were prepared from intestinal mucosa of patients with DD, UC or CD, from histologically normal mucosa adjacent to cancerous tissue, and from polyps and carcinoma tissues.

Telomerase assay

Extracts were prepared from frozen tissues stored at −80° C. by powdering the tissue under liquid nitrogen, followed by addition of 2 $\mu$l of ice-cold lysis buffer [10 mM Tris-HCl (pH 7.5), 1 mM $MgCl_2$, 1 mM EGTA, 1 mM PMSF, 5 mM β-mercaptoethanol, 0.5% CHAPSO, 10% glycerol] per mg of powder (Kim et al., (1994)). The cell suspension was incubated for 30 min on ice with occasional mixing before centrifugation at 100,000 g for 30 min at 4° C. Extracts of 293 cells were prepared by scraping 293 cells cultured to subconfluency on 1–2 150 mm dishes, after rinsing twice with ice-cold phosphate-buffered saline lacking calcium and magnesium. The cells were collected by centrifugation, resuspended in ice-cold wash buffer [10 mM HEPES-KOH (pH 7.5), 1.5 mM $MgCl_2$, 10 mM-KCl, 1 mM DTT], pelleted again, resuspended in 15 $\mu$l of ice-cold lysis buffer per $10^6$ cells and processed as for tissues extracts. Supernatants were aliquoted, flash-frozen in liquid nitrogen and stored at −80° C. Protein concentration was determined by the Bradford assay (Bio-Rad). Control samples were pre-treated with RNase to a final concentration of 0.05 mg/ml for 10 minutes at room temperature. The Telomeric Repeat Amplification Protocol (TRAP; Kim et al., (1994)) was used for telomerase assays which is capable of detecting activity in as few as 10 positive cells or as little as 0.01% positive cells in a mixed population. Aliquots of extracts were incubated with 0.1 $\mu$g TS oligonucleotide (5'-AATCCGTCGAGCAGAGTT-3') (SEQ ID NO:6) for 10 min at room temperature in 20 mM Tris-HCl pH 8.3, 1.5 mM $MgCl_2$, 63 mM KCl, 0.005% Tween 20, 1 mM EGTA, 50 $\mu$M each dNTP, 0.5 mM T4-gene 32 protein, 2 $\mu$Ci$\alpha^{32}$PdCTP (3000 Ci/mmol), to allow for elongation of the TS primer by telomerase. The reactions were warmed to 92° C. prior to addition of 2 U of Taq polymerase and 0.1 Kg of the CX primer (5'-CCCTTACCCTTACCCTTACCCTAA-3') (SEQ ID NO:7) and the elongated products were amplified by PCR through 30 cycles at 94° C. for 30 seconds, 50° C. for 30 seconds and 72° C. for 90 seconds. Initial assays were performed at 30 PCR amplification cycles using 20 $\mu$g of protein, except in the case of 3 very small polyps which were assayed at 5 or 10 $\mu$g protein (Table 2). The assay can be improved by using end-labelled TS primer and by replacing the CX primer with the ACT oligonucleotide (5'-GCGCGGCTAACCCTAACCCTAACC-3') (SEQ ID NO:8), which is unable to dimerize to TS and anneals at 60° C. These two modifications increased both the specificity and the sensitivity of the assay. Products from half of each reaction were resolved in 15% non-denaturing polyacrylamide gels and visualized after exposure to Phosphor-Imager screens, using limits of sensitivity of 5000–50000 counts for the most active samples (293 and C17), 1000–10000 counts for samples with intermediate activity (C18, C19 and 307), and 500–1500 counts for the least active sample (314). Extracts were considered negative if no telomerase products were detected upon a 3 day exposure. As dilution of highly positive extracts, such as those from 293 cells, was found to enhance the level of enzymatic activity, telomerase negative tissue extracts were re-assayed using 0.2 $\mu$g protein. Inhibition of telomerase activity at high protein concentrations appears to be characteristic for the PCR-based TRAP assay, as activity of the 293 cell line was found to be proportional to protein amounts ranging from 2 to 200 $\mu$g using the conventional assay (Counter et al., (1994b). Enzymatic activity was detected as a 6 nucleotide repeat ladder that was sensitive to pre-treatment of the extracts with RNase for the immortal human 293 cell line, used as a positive control.

Results for all patient samples are summarized in Table 2. Enzyme activity was not detected in any sample of histologically normal mucosa, whether from cancer or non-cancer patients. Similarly, all of the 21 polyps from 15 different patients were found to be telomerase negative. Lack of enzymatic activity in negative extracts was confirmed in all cases by assaying at 100 fold lower protein concentration. In contrast, enzymatic activity was detected in 14 of 15 adenocarcinomas. Activity in these samples was detectable only by assaying 20 $\mu$g protein and was lower than that of 293 cells, except for one case where activity was comparable to that of 293 cells and was enhanced by dilution of the extract (not shown). Lack of telomerase activity in the single negative sample of adenocarcinoma was confirmed by assaying a different section of the biopsy and again by dilutions of the extracts. Although this sample was about 20% necrotic, it had similar levels of DNA polymerase activity as telomerase positive tumors, nor differed from them in other clinical characteristics or in donor's age. Lack of telomerase activity may be related to degradation of the telomerase.

Telomerase activity was not detected in histologically normal liver from 4 patients presenting with liver metastases from a previously resected colonic tumor. However, one of two biopsies from a fifth patient was positive, perhaps due to the presence of micrometastases. Two independent samples of liver metastases from 5 patients were also negative, except for a single patient (Table 2). As liver abounds in degradative enzymes and moreover is devascularized during surgery for a significantly longer period of time than colon (2–3 hours versus 20–30 min), another replicative enzyme was assayed. Three of the four telomerase negative extracts had no detectable DNA polymerase activity, and in-the fourth the levels of this enzyme were about 6-fold lower than in positive tumors. Even the single telomerase positive metastasis had reduced DNA polymerase activity, but only by about 3-fold. These results are compatible with generalized protein degradation as the cause for the lack of detectable telomerase activity in liver metastases.

DNA analysis

Terminal restriction fragments (TRFs), comprising telomeric and subtelomeric DNA, were obtained from genomic DNA by digestion with restriction enzymes, resolved in 0.5% agarose gels and visualized by hybridization with a telomeric specific probe, as previously described (Counter et al., (1992)). Following exposure to Phosphor-Imager screens (Molecular Dynamics, Sunnyvale, Calif.), mean TRF length was calculated from the total counts between 21 and 2 kbp, determined by using ImageQuant software (Molecular Dynamics).

TRFs were measured in a matched series of normal mucosa and 11 polyps from 8 patients. TRFs in polyps varied in length, being shorter (5/11), comparable (2/11) or longer (4/11) than in control tissue. The latter polyps were from 2 patients with unexpectedly short TRFs in normal mucosa for their age. Variability in TRFs of polyps is likely to reflect clonal variation, since all samples were negative for telomerase and polyp size was not sufficiently different to account for differences in TRFs length.

TABLE 2

| Patient Code | Diagnosis* | Age | Staging† | Differentiation | Location | Telomerase Activity‡ NM | P | T | NL | LMets |
|---|---|---|---|---|---|---|---|---|---|---|
| *Non malignant diseases* | | | | | | | | | | |
| 217 | DD | 46 | | | colon | – | | | | |
| 274 | DD | 47 | | | colon | – | | | | |
| 309 | DD | 74 | | | colon | – | | | | |
| 218 | CD | 52 | | | colon | – | | | | |
| 316 | UC | 31 | | | colon | – | | | | |
| C1 | FAP | 38 | | | rectum | – | – | | | |
| C2 | FAP | 29 | | | colon | – | –, – | | | |
| C3 | FAP | 23 | | | colorectum | – | –, – | | | |
| C5 | FAP | 44 | | | colon | | – | | | |
| C7 | FAP | 19 | | | colon | – | –, – | | | |
| C8 | FAP | 20 | | | colon | – | –, – | | | |
| C9 | FAP | 41 | | | colon | – | | | | |
| C10/11 | FAP | 60 | | | duodenum | | – | | | |
| C12/13 | FAP | 63 | | | duodenum | | –, – | | | |
| C14/15 | FAP | 55 | | | duodenum | | –, – | | | |
| C20 | AdP | 58 | | | colon | – | – | | | |
| *Malignant diseases* | | | | | | | | | | |
| 307 | ACA | 59 | T3N0 | moderate | colon | – | – | + | | |
| 314 | ACA | 69 | NA | well/mod. | colorectum | – | – | + | | |
| C4 | ACA | 85 | T3N0 | NA | colon | – | – | + | | |
| C6 | ACA | 65 | NA | moderate | colon | – | – | | | |
| 008 | ACA | 74 | T4N0 | moderate | colon | – | | + | | |
| 013 | ACA | 85 | T4NX | NA | colon | – | | + | | |
| C17 | ACA | 80 | NA | moderate | colon | – | | + | | |
| C18 | ACA | 75 | T3N1 | NA | colon | – | | + | | |
| C19 | ACA | 65 | T4N1 | NA | colon | – | | + | | |
| C21 | ACA | 79 | T3N3 | moderate | colon | – | | – | | |
| C26 | ACA | 75 | T3N1 | moderate | colon | – | | + | | |
| C27 | ACA | 29 | NA | moderate | rectum | – | | + | | |
| C28 | ACA | 56 | T2N2 | moderate | rectum | – | | + | | |
| C29 | ACA | 66 | T3N0 | moderate | rectum | – | | + | | |
| C30 | ACA | 46 | T4N2 | mod./poor | colon | – | | + | | |
| C31 | ACA | 80 | T2N0 | moderate | colon | – | | + | | |
| C16 | ACA | 64 | | | liver | | | | – | –, – |
| C22 | ACA | 58 | | | liver | | | | –, – | –, – |
| C23 | ACA | 62 | | | liver | | | | –, – | –, – |
| C24 | ACA | 70 | | | liver | | | | +, – | +, + |
| C25 | ACA | 50 | | | liver | | | | –, – | –, – |
| Total. # positive/# patients | | | | | | 0/26 | 0/15 | 14/ | 1*/5 | 1/5 |
| n = # polyps | | | | | | | n = 21 | 15 | | |

*DD: diverticular disease; CD: Crohn's disease; UC: ulcerative disease; FAP: familial adenomatous polyposis; AdP: adenomatous polyps (sporadic); ACA: adenocarcinoma.
†According to the AJCC/UICC classification.
‡All samples were tested at 20 μg protein except for samples C12/13 and C14/15 which were tested at 5 or 10 μg. Negative samples were retested at 0.2 μg NM: normal mucosa; P: polyp; T: primary tumor; NL: normal liver LMets: liver metastases well/mod. well to moderately differentiated; mod./poor: moderately to poorly differentiated.
NA: not available from tissue report.
*For the total, patient C24 was considered positive although this was the case for only 1 of 2 samples.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

---

What is claimed is:

1. A method for detecting myelodysplastic syndrome, said method comprising:
   (a) collecting a bone marrow sample;
   (b) analyzing said sample for telomerase activity;
   (c) correlating said activity with a first standard level and a second standard level of telomerase activity, wherein said first standard level of telomerase activity is at least 4-fold less than said second standard level of telomerase activity; and
   (d) correlating a telomerase activity falling within said first and said second standard levels of telomerase levels of telomerase activity with myelodysplastic syndrome.

2. A method for differentiating between early and late stage leukemia, said method comprising:
   (a) collecting a blood or bone marrow sample from an individual having leukemia;
   (b) analyzing said sample for telomerase activity;
   (c) correlating said activity with a standard level of telomerase activity; and
   (d) correlating a low telomerase activity with early stage leukemia and a high telomerase activity with late stage leukemia, wherein said low telomerase activity in early stage leukemia is at least 2-fold less than said high telomerase activity in late stage leukemia.

3. The method of claim 1, wherein said first standard level is a level of telomerase activity in a normal bone marrow sample.

4. The method of claim 3, wherein said second standard level of telomerase activity is 4-fold more than said first standard level of telomerase activity.

5. The method of claim 1, wherein said second standard level is a level of telomerase activity in an AML-diseased bone marrow sample.

6. The method of claim 1, wherein said analyzing in step (b) comprises preparing a cell extract.

7. The method of claim 1, wherein said analyzing step comprises incubating said aliquot in a reaction mixture comprising a telomerase substrate and a buffer in which telomerase can catalyze the extension of said telomerase substrate, and determining whether said telomerase substrate has been extended by addition of telomeric repeat sequences.

8. The method of claim 7, wherein said analyzing step further comprises amplifying any extended telomerase substrates in said reaction mixture by a polymerase chain reaction using at least one primer complementary to a telomeric repeat sequence.

9. The method of claim 8, wherein said analyzing step further comprises amplifying a control oligonucleotide in said reaction mixture by a polymerase chain reaction.

10. The method of claim 2, wherein said sample is a blood sample.

11. The method of claim 2, wherein said sample is a bone marrow sample.

12. The method of claim 2, wherein said early stage leukemia is myelodysplastic syndrome and said late stage leukemia is acute myeloid leukemia, and said low telomerase activity in step (d) exceeds telomerase activity levels present in a normal bone marrow sample.

13. The method of claim 2, wherein said leukemia is chronic lymphoid leukemia.

14. The method of claim 13, wherein said standard level is a level of telomerase activity in normal leucocytes and said low telomerase activity is less than said standard level.

15. The method of claim 2, wherein said analyzing in step (b) comprises preparing a cell extract.

16. The method of claim 2, wherein said analyzing step comprises incubating said aliquot in a reaction mixture comprising a telomerase substrate and a buffer in which telomerase can catalyze the extension of said telomerase substrate, and determining whether said telomerase substrate has been extended by addition of telomeric repeat sequences.

17. The method of claim 16, wherein said analyzing step further comprises amplifying any extended telomerase substrates in said reaction mixture by a polymerase chain reaction using at least one primer complementary to a telomeric repeat sequence.

18. The method of claim 17, wherein said analyzing step further comprises amplifying a control oligonucleotide in said reaction mixture by a polymerase chain reaction.

19. The method of claim 12, wherein said low telomerase activity in step (d) exceeds telomerase activity levels present in said normal bone marrow sample by at least 2-fold but by less than 4fold.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:

( A ) LENGTH: 23 base pairs
            ( B ) TYPE: nucleic acid
            ( C ) STRANDEDNESS: single
            ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:1:

CCCAATCCGT CGAGCAGAGT TAG                                                23

( 2 ) INFORMATION FOR SEQ ID NO:2:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:2:

TAACTCTGCT CGACGGATTC CC                                                 22

( 2 ) INFORMATION FOR SEQ ID NO:3:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:3:

GGGTAACCCT AACCCTAACC C                                                  21

( 2 ) INFORMATION FOR SEQ ID NO:4:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:4:

GGTTAGGGTT AGGGTTAAA                                                     19

( 2 ) INFORMATION FOR SEQ ID NO:5:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:5:

CCCTAACCCT AACCCTAA 18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:6:

AATCCGTCGA GCAGAGTT 18

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:7:

CCCTTACCCT TACCCTTACC CTAA 24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:8:

GCGCGGCTAA CCCTAACCCT AACC 24

( 2 ) INFORMATION FOR SEQ ID NO:9:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:9:

AATCCGTCGA GCAGAGTTGG TTAGGGTTAG GGTTAGGGTT AGGGTTAGGG TTAGGGTTAG        60